(12) United States Patent
Harada et al.

(10) Patent No.: US 8,399,414 B2
(45) Date of Patent: Mar. 19, 2013

(54) ANALGESICS

(75) Inventors: Etsumori Harada, Tottori (JP); Takashi Takeuchi, Tottori (JP); Kenichiro Hayashida, Tottori (JP); Kunio Ando, Kanagawa (JP); Hirohiko Shimizu, Shizuoka (JP)

(73) Assignee: NRL Pharma, Inc. (JP)

( * ) Notice: Subject to any disclaimer, the term of this patent is extended or adjusted under 35 U.S.C. 154(b) by 0 days.

(21) Appl. No.: 10/502,209

(22) PCT Filed: Jan. 17, 2003

(86) PCT No.: PCT/JP03/00350
§ 371 (c)(1),
(2), (4) Date: Feb. 9, 2005

(87) PCT Pub. No.: WO03/061688
PCT Pub. Date: Jul. 31, 2003

(65) Prior Publication Data
US 2005/0119162 A1 Jun. 2, 2005

(30) Foreign Application Priority Data
Jan. 21, 2002 (JP) .................................. 2002-11914

(51) Int. Cl.
*A61K 38/40* (2006.01)
*C07K 14/79* (2006.01)
(52) U.S. Cl. ....... 514/18.3; 514/18.4; 530/350; 530/395
(58) Field of Classification Search ........................ None
See application file for complete search history.

(56) References Cited

U.S. PATENT DOCUMENTS

| | | | |
|---|---|---|---|
| 4,918,008 A | 4/1990 | Gauri | |
| 5,317,084 A | 5/1994 | Tomita et al. | |
| 6,204,271 B1 * | 3/2001 | Fairbanks et al. | 514/269 |
| 6,224,910 B1 * | 5/2001 | Ullah et al. | 424/489 |
| 2003/0096736 A1 * | 5/2003 | Kruzel et al. | 514/6 |
| 2005/0119162 A1 | 6/2005 | Harada et al. | |

FOREIGN PATENT DOCUMENTS

| | | |
|---|---|---|
| EP | 0 730 868 | 9/1996 |
| EP | 0 955 058 | 11/1999 |
| JP | 2001-48804 | 2/2001 |
| JP | 2001-48808 | 2/2001 |
| JP | 2001-354583 | 12/2001 |
| RU | 2088238 C1 | 8/1997 |
| WO | WO 91/04015 | 4/1991 |
| WO | WO 93/13790 | 7/1993 |
| WO | WO 9313790 * | 7/1993 |
| WO | WO 98/44940 | 10/1998 |
| WO | WO 9844940 * | 10/1998 |
| WO | WO 00/22909 | 4/2000 |

OTHER PUBLICATIONS

Nakajima, M., et al. 1999. Oral Administration of Lactoferrin Enhances the Productions of IFN-gamma and IL-10 in Spleen Cells Cultured with Concanavalin A or Lipopolysaccharide. Biomedical Research 20(1): 27-33.*
Bass, J., Drink Milk Tip from about.com.*
Hazum, E., et al. Morphine in Cow and Human Milk: Could Dietary Morphine Constitute a Ligand for Specific Morphine (u) Receptors. Aug. 28, 1981 Science 213(4511): 1010-1012.*
Fiat, A.-M., et al. 1993 J Dairy Sci 76: 301-310.*
Oberlander, T.F., et al. 2000 J Hum Lact 16(2): 137-142.*
NCI reference sheet (1 page).*
Stefano, G.B., et al. 2000 Trends in Neuroscience 23(9): 436-442.*
Sluka, K.A., et al. 1998 Pain 77: 97-102.*
Galaev, I.Y., et al. 2002 Biotechnology Applications, Encyclopedia of Polymer Science and Technology: 25 pages.*
Mitsunari Nakajima et al.; "Oral Administration of Lactoferrin Enhances the Productions of IFN-y and IL-10 in Spleen Cells Cultured with Concanavalin A or Lipopolysaccharide"; Biomedical Research 1999, vol. 20 (1), pp. 27-33.
Wakabayashi, Hiroyuki et al., "No Detectable Transfer of Dietary Lactoferrin or Its Functional fragments to Portal Blood in Healthy Adult Rats", Biosci. Biotechnol, Biochem., 68 (4), pp. 853-860, 2004.
Takeuchi, Takashi et al., "Enteric-formulated lactoferrin was more effectively transported into blood circulation from gastrointestinal tract in adult rats", Exp Physiol 91.6 pp. 1033-1040, 2006.
Hayashida, Ken-Ichiro et al., "Lactoferrin enhances opioid-mediated analgesia via nitric oxide in the rat spinal cord", Am J Physiol Regul Integr Comp Physiol 285; R306-R312, 2003.
Stefano, George B. et al., "Endogenous morphine", Trends in Neurosci, No. 9, (23), pp. 436-442, 2000.
Supplementary European Search Report for Application No. 0370059.2-2112 / 1477182 PCT/JP0300350 mailed Apr. 24, 2009.

(Continued)

*Primary Examiner* — Marsha Tsay
(74) *Attorney, Agent, or Firm* — Cantor Colburn LLP

(57) ABSTRACT

The object of this invention is to provide a novel pharmaceutical composition for getting rid of pains and anxiety in patients. This invention relates to a pharmaceutical composition containing lactoferrin as an active ingredient. The composition of this invention is useful for treatment of at least one disease or condition selected from the group consisting of pains, including the phase 1 pain and the phase 2 pain, anxiety and stress. The composition is particularly beneficial to alleviating or getting rid of the pain and anxiety which significantly lower quality of life of patients with end-stage cancer. The composition of this invention is also useful for treatment of pains, including the phase 1 pain and the phase 2 pain, and inflammation which accompany arthritis or diseases in the junctions of bones (e.g. rheumatoid arthritis, osteoarthritis, frozen shoulder, sports injuries such as tennis elbow and baseball shoulder, and low back pain).

20 Claims, 13 Drawing Sheets

OTHER PUBLICATIONS

Database WPI Week 199826, Thomson Scientific, London, GB; AN, 1998-295478, Aug. 27, 1997; Abstract.

Rocco, A., et al.: A double-blind comparison of epidural steroids and epidural steroids combined with morphine in the treatment of reccurent low back pain.:, PAIN, Elsevier Science Publishers, Amsterdamn, NL., vol. 30, Jan. 1, 1987, p. S118; Abstract.

Guillen, C., et al.: "The Effects of Local Administration of Lactoferrin on Inflammation in Murine Autoimmune and Infectious Arthritis", Arthritis and Rheumatism, Lippincott, Philadelphia, US, vol. 43, No. 9. Jan. 1, 2000.

Machnicki, M., et al.: "Lactoferrin Regulates the Release of Tumour Necrosis Factor Alpha and Interleukin 6 in Vivo", International Review of Experimental Pathology, Blackwell Scientific, Oxford, GB, vol. 74, No. 5., Jan. 1, 1993, pp. 433-439, XP009006113.

Takeuchi, Takashi et al., "Enteric-formulated lactoferrin was more effectively transported into blood circulation from gastrointestinal tract in adult rats", (Received Jun. 24, 2006; accepted after revision Sep. 1, 2006; first published online Sep. 7, 2006) (c) 2006 The Authors, Journal Ccompilation (c) 2006 The Physiological Society; Exp Physiol 91, 6 pp. 1033-1040.

Lactoferrin Lecture Highlight by Michael Rosenbaum, MD; NutriCology.com; found at: htt;://www.nutricology.com/proddesc/experts/LectureHighlightLactoferrin.pdf, accessed Jan. 10, 2007.

Arthritis Care Paper "Arthritis Care: Medication" located at http://www.arthritiscare.org.uk/AboutArthritis/Treatments/Medication; downloaded Oct. 13, 2010, 2 pgs.

Bass, Jesslyn Drink Milk—Runners' Weight Loss Tips, located at http://running.about.com/od/weightlosstips/qt/milk.htm, dated Feb. 3, 2006, 2 pgs.

Reply to Office Action for Canadian Application No. 2,471,766, filed on Dec. 27, 2002; for Compsoitions for Improving Lipid Metabolism, dated Aug. 11, 2010, 19 pgs.

Canadian Office Action for Application 2,476,984, dated Mar. 5, 2010, 6 pages.

Reply to Office Action re Canadian Patent Application No. 2,476,984; filed on Jan. 17, 2003; Lactoferrin as an Agent for Enhancing Action of an Opioid (formerly Novel Analgesics), dated Sep. 7, 2010, 17 pgs.

Hayashida, Ken-ichiro et al., "Novel function of bovine milk-derived lactoferrin on antinociception mediated by m-opioid receptor in the rat spinal cord", Science Direct, Brain Research 965 (2003) pp. 239-245.

Hayashida, Ken-ichiro et al., "Oral Administration of Lactoferrin Inhibits Inflammation and Nociception in Rate Adjuvant-Induced Arthritis", received Jun. 9, 2003, Accepted Sep. 17, 2003; Full Paper Physiology, J. Vet. med. Sci. 66(2): pp. 149-154, 2004.

Hayashida, Ken-ichiro et al., Lactoferrin enhances peripheral opioid-mediated antinociception via nitric oxide in rats, available online at www/sciencedirect.com; European Journal of Pharmacology 484 (2004, pp. 175-181.

Heggestad, Howard E., et al. Morphine in Cow and Human Milk: Could Dietary Morphine Constitute a Ligand for Specific Morphine (m) Receptors?, Science, vol. 213, Aug. 28, 1981, pp. 1010-1012.

Kamemori, Nao, et al., Suppressive effects of milk-derived lactoferrin on psycholoogical stress in adult rats; accepted Sep. 21, 2004; available online Oct. 27, 2004; located online at www.sciencedirect.com; Brain Research 102 (2004), pp. 34-40.

Miyauchi, Hirofumi, et al. "Immunomodulatory Effect of Bovine Lactoferrin Pepsin Hydrolysate on Murine Splenocytes and Peyer's Patch Cells" 1997, J. Dairy Sci.: 80, pp. 2330-2339.

Shimazaki, Kei-ichi et al., "Lactoferrin: Structure, Function and Applications", Proceedings of the 4th International Conference on Lactoferrin: Structure, Function and Applications, held in Sapporo, Japan, May 18-22, 1999, 2000 Elsevier, cover pg, pp. 415-427.

Takeuchi,Takashi et al., Opioid mediated suppressive effect of milk-derived lactoferrin on distress induced by maternal separation in rat pups, available online at www.sciencedirect.com; Brain Research 979 (2003) pp. 216-224.

Takeuchi,Takashi et al. "Evidence fo lactoferrin transportation into blood circulation from intestine via lymphatic pathway in adult rats", Exp. Physiol. 89.3, pp. 263-270, 2004.

Teschemacher, Hansjorg "Lactoferrin elicits opioid-mediated antinociception without development of tolerance: central nNOS-1 set off duty?", Am J. Physiol Regulatory Integrative Comp Physiol 285: cover page, pp. R302-R305, 2003.

Tsuchiya, Tomohito et al., "Milk-derived lactoferrin may block tolerance to morphine analgesia", available at www.scienedirect.com; Brain Research, 1068 (2006), pp. 102-108.

Wagner, John J., et al. "Neuropharmacology of Endogenous Opioid Peptides", Neuropsychopharmacology: The Fifth Generation of Progress, web page located at http://www.acnp.org/g4/gn401000050/ch050.html, downloaded Jun. 25, 2010, published 2000.pp. 1-11.

Wikipedia "Pain management" located at http://en.wikipedia.org/wiki/Pain_management, downloaded Sep. 8, 2010, 10 pgs.

Wikipedia, Tablet—located at http://en.wikipedia.org/wiki/Tablet, downloaded Oct. 12, 2010, 7 pages.

\* cited by examiner

Control-1

Control-2

Adjuvant-1

Adjuvant-2

Adjuvant+LF-1

Adjuvant+LF-2

ANALGESICS

This application is a national stage U.S. application filed under 35 U.S.C. 371 of International application PCT/JP03/00350, filed Jan. 17, 2003, which claimed the priority of Japanese Patent 2002-11914 filed Jan. 21, 2002, the disclosures of which are incorporated herein in its entirety by reference.

TECHNICAL FIELD

The present invention relates to a pharmaceutical composition containing lactoferrin. The composition of this invention is useful for treatment of at least one disease or condition selected from the group consisting of pains including phase 1 and phase 2 pains, anxiety and stress. The composition is particularly useful for alleviating or getting rid of pain and anxiety in patients with end-stage cancer, which significantly lower the quality of life of the patients. The composition of this invention is also useful for treatment of pains, including phase 1 pain and phase 2 pain, and inflammation which accompany arthritis or diseases in junctions of bones (e.g. rheumatoid arthritis, osteoarthritis, frozen shoulder, sports injuries such as tennis elbow and baseball shoulder, and low back pain).

BACKGROUND ART

"Cancer" has been the leading cause of death in Japanese people since 1981, and is steadily increasing year by year with the coming of an aging society. The incidence of pain in cancer patients, which inflicts unbearable agony on the patients, increases with the worsening of their condition, and 80% of patients with end-stage cancer suffer from persistent severe pain and fall into extreme anxiety in fear of death.

Since most of anxiety-ridden feeling comes from pain, WHO has proposed that analgesic used for treatment of pain associated with cancer be divided into 3 groups according to the stages of pain. The analgesic used for final-stage pain are morphine and the like. The analgesic used for alleviating relatively mild first-stage pain are non-narcotic analgesic, such as acetaminophen, aspirin and ibuprofen, and drugs for controlling special pain or other symptoms, such as antidepressant, antiepileptic, antiemetic and antianxiety drug, are also used as adjuvant drugs. To control moderate second-stage pain, weak narcotic analgesic are concurrently used with other analgesic. Typical examples of weak narcotic analgesic are codein and oxycodone-combined drug. In order to set patients free from unbearable final-stage pain associated with cancer, various morphine formulations have been developed. In the meantime, to get rid of anxiety of patients, glucocorticoid formulations (commonly known as steroid), as an anti-stress hormone, have been frequently used.

The reasons why appropriate treatment for pain is absolutely necessary are not only that setting patients free from pain improves patients' quality of life (QOL), but that pain causes patients to lose the energy to fight against diseases. Imperfect treatment for pain causes patients to be in anxiety, and hence to lose the energy to fight against cancer and receive treatment for cancer. If treatment for cancer cannot alleviate patients' pain sufficiently, the foundation of the treatment can be very questionable. A very important point is that pain is unnecessary, which simply worsens the condition of patients. Treatment for pain should be considered to be a problem of great urgency and not be deferred for future discussion. In other words, treatment for severe pain is as important as treatment for cancer itself. Pain largely affects the condition of patients, and therefore treatment for pain should not be distinguished from treatment for cancer. The two cannot be separated from each other.

A sensation of pain is highly apt to be influenced by a state of mind, and patients with cancer feel less pain when they spend their time with their family at home while feeling the rhythm of the day and that of the week. Treatment for pain is more effective at home, if possible, than in hospital. However, the question about treatment for cancer at home is that the usage of morphine and steroid has not been commonly known to the lowest levels of medical institutions. There are many cases where a patient is treated by an expert in a specialized medical institute and recovers his or her appetite by administration of steroid, but once the patient is discharged from the institute and sees a non-specialist in a local hospital, the non-specialist regards taking steroid as dangerous and stops the patient from taking steroid. Since morphine and steroid are drugs that needs care upon use, discontinuation of their administration cannot be rejected in a wholesale manner as a wrong measure.

The reason that morphine and steroid can be used without restriction in treatment of cancer is that they are used as part of the terminal care that sets patients free from pain and anxiety and allows them to die with dignity as human beings.

However, the abuse of morphine makes patients lapse into drug dependence and it is significantly difficult for the patients to recover from their drug dependence. Further, morphine inhibits the intestinal peristalsis, and therefore morphine-treated patients come to have abdominal distention and severe constipation. Patients with cancer have smaller food ingestion due to a poor appetite compared with healthy individuals and treatment with morphine causes them to have severe constipation, and thus it is no rare matter that they have only one bowel movement for 7 to 10 days. Long retention of old stools in the body inevitably affects the normal metabolic and immunological functions. A laxative is mainly prescribed for the constipation caused by morphine, but its efficacy is limited. No morphine formulations which do not cause constipation have come into existence yet. Morphine is also known to cause vomiting. It is reported that the incidence of vomiting by morphine does not differ depending on the route of morphine administration, it is one third in morphine-treated patients, and that only one third of morphine-treated patients need not co-administration of an antiemetic with morphine. Such a high incidence of vomiting gives rise to even an opinion that all the morphine-treated patients should be co-administered an antiemetic with morphine when the morphine administration is started. In many morphine-treated patients, the time when they need an antiemetic is about 2 weeks after the start of morphine administration, since the resistance to emetic action appears relatively early; however, the escalation of health care cost due to the concomitant treatment is problematic. In addition, there is a side effect, drowsiness, in about 20% of morphine-treated patients. Other side effects are also observed associated with morphine, such as respiration depression, confusion, hallucination, lightheaded feeling, pressure reduction, perspiration and pruritus. Mouth dryness found in about half of morphine-treated patients is a side effect that seriously lowers the QOL. These side effects not only cause patients to have an unwell feeling, but also act as a pressure to escalate health care cost.

Steroid used as an anti-stress hormone also has various side effects. The side effect on which most careful watch should be kept is an immunosuppressive effect. The main cause of death in patients with cancer is said to be multiple organ failure which is caused by the invasion of opportunistic pathogen due to the decrease in immunopotency of the patients. Accordingly, the possibility cannot be denied that steroid, which decreases the immunopotency of patients, shortens the patients' lives. In addition, due to its strong catabolism, steroid probably accelerates the debility of patients and therefore shortens their lives. Other side effects of steroid include: for example, anasarca and urinary retention due to the suppression of sodium excretion in urine; and fracture due to the acceleration of calcium elution from bone.

Even when the pain and anxiety in patients with cancer are excellently controlled, it is no rare thing that their condition takes a sudden turn for the worse in a very short period of time. This is called cancerous symptoms of urgency. Cancerous symptoms of urgency include: for example, dyspnea, increase in pain, disturbance of consciousness/derangement, urinary retention, fracture, hemorrhage, paralysis/weakness of upper extremities, and paralysis of one side of the body. These symptoms are probably related to the overdosage of morphine and steroid.

Control of pain caused by cancer and of patients' anxiety accompanying the pain is medical care in an extreme situation, and there are a large number of diseases other than cancer that require control of pain and anxiety. In other words, getting rid of pain and anxiety accompanying the pain occupies an important position in medical care. Thus, a social need is very strong for means which can improve pain and get rid of anxiety at low cost, while avoiding such side effects that morphine and steroid have.

In the mean time, pain or low back pain which accompanies arthritis is also a serious problem. Typical examples of arthritis are rheumatoid arthritis, osteoarthritis, frozen shoulder, and arthritis caused by sports injuries. Low back pain is pain in junctions of bones.

Rheumatoid arthritis is a chronic inflammatory disease that causes polyarthritis, the disease is more than 3 times as common in females as in males, and it is said that the incidence is high in their 30s to 50s. Of the factors contributing to the onset of the disease, the following three factors: inborn pre-disposition, immunological factors and circumstance are regarded as important. It is said, with respect to the immunological factors, that rheumatoid factor synthesized in the joints binds to immunoglobulin G to cause arthritis, which leads to the progression of joint destruction. The circumstance includes, for example, chill, humidity, stress and infection with virus. Early symptoms consist mainly of stiff joints when waking up in the morning, joint pain and joint swelling. Frequently affected joints are those of the finger and toe, wrist, ankle, elbow, knee and shoulder and when the disease has progressed, they can sometimes be deformed. The disease may cause systemic symptoms such as feeling of weakness, lassitude and low-grade fever, besides symptoms in joints. Once affected with rheumatoid arthritis, patients are hard to be perfectly cured and have to live with the disease throughout their lives. To prevent the worsening of the disease, patients need to try to rest both mind and body, do moderate exercise, take in nutrients such as vitamins, minerals and proteins, and defend themselves against the cold and humidity.

Osteoarthritis is a non-inflammatory disease which causes little by little the deformation of the diarthrosis, in particular, joints to which loads are applied, and hence pain and limited range of motion in such joints. The disease is characterized pathologically by the destruction of articular cartilage and the osteogenesis of subchondral bone. The disease is classified into two: a primary osteoarthritis which is developed with aging; and a secondary osteoarthritis which is developed with underlying diseases such as injuries and rheumatoid arthritis. The pathogeny and the mechanism of osteoarthritis are thought to be as follows. Primary osteoarthritis is a symptom of senility in articular cartilage which is developed by mechanical impact probably under the influence of aging, metabolic disorder, circulatory disorder, obesity and sex hormone. Underlying diseases which may cause secondary osteoarthritis include, for example, injuries, rheumatoid arthritis, alkaptonuria, hemochromatosis, gout and Charcot joint. More than half of the adults are said to have secondary osteoarthritis and the incidence of the disease increases with aging in a geometric series manner. Those in 60s or more without the disease, including a mild case, are unusual. The disease is almost as common in males as in females.

Frozen shoulder, tennis elbow, baseball shoulder and various types of low back pain are also characterized by the pain occurring in the junctions of bones, and thus classified as diseases of joint. The pain caused by these diseases might not threaten the patient lives, but is generally intractable and takes a chronic course.

At present, drugs usually prescribed to alleviate the pain caused in the joints by rheumatoid arthritis, osteoarthritis, etc. or the pain caused in the junctions of bones such as low back pain include, for example, several tens of synthetic compounds referred to as non-steroidal analgesic or antiphologistics, such as aspirin, indomethacin, ibuprofen and diclofenac and synthetic glucocorticoid hormone etc. referred to as steroid.

Pain is mediated by prostaglandin, and if the biosynthesis of prostaglandin is decreased/stopped by inhibiting cyclooxygenase with a non-steroidal antiinflammatory drug, pain is alleviated. However, since prostaglandin influences hemodynamics in stomach, if its synthesis in stomach is inhibited, peptic ulcer is caused frequently in the stomach whose blood flow is decreased. Conventional non-steroidal antiinflammatory drugs are double-edged swards which inhibit both cyclooxygenase-1 and cyclooxygenase-2 as rate-limiting enzymes in the synthesis of prostaglandin. A current topic in the field of non-steroidal antiinflammatory drugs is the advent of cox-2 inhibitor that inhibits specifically the cyclooxygenase-2 (cox-2) developing in the inflammatory regions. The cox-2 inhibitor is expected to make it possible to decrease peptic ulcer, which has been an inevitable result of the use of non-steroidal antiinflammatory drugs.

Glucocorticoid (what is called steroid) as an adrenal cortical hormone is also frequently used for treatment of arthritis. Although steroid provides a dramatic improving effect on arthritis, its use is significantly limited due to the incidence of various side effects. Treatment with steroid causes serious side effects in patients; for example, it decreases the immunopotency of the patients and causes the patients to be susceptible to infectious diseases, frequently causes peptic ulcer, and induces diabetes in the patients. In addition, discontinuation of its administration causes rebound phenomenon that the symptoms are worsened before administration.

Gold preparation, penicillamine, immunosuppressive drug and antiinterleukin-6 antibody are also used for treatment of arthritis, but their prescription is restricted within narrow limits.

Pain in joints, even pain accompanying frozen shoulder, low back pain or sport injuries which have good chances of being cured, is characterized by its taking a chronic course. And in rheumatoid arthritis and osteoarthritis, it is very difficult for patients to make a complete recover from the diseases and once affected with the diseases, the patients are to live with the diseases throughout their lives. To allow pain in joints to subside, patients can be given physical therapy such as balneotherapy, but the mainstream is medicinal treatment with non-steroidal antiinflammatory drugs and steroid. As aforementioned, these drugs induce peptic ulcer with a high frequency following long-term administration. Thus, a method has long been sought of improving pain in joints in high safety while avoiding the induction of peptic ulcer.

Lactoferrin is an iron-binding protein existing in milk of various kinds of mammals. It was first discovered in bovine's milk in 1939 and found later to exist in milk of many kinds of mammals other than bovine. In 1960 it was first isolated from milk of bovine and human beings, and its structure was determined by Baker et al. using X-ray diffraction method (Baker et al. Proc. Natl. Acad. Sci. USA 84: 1769-1773, 1987). In human beings, lactoferrin is isolated not only from milk, but also exocrine fluids such as tears, nasal discharge, saliva, bronchial and uterine mucus, seminal fluid, bile and pancreatic fluid; body fluids such as blood plasma, urine and amniotic fluid; and secondary granules of neutrophil, and about 5 g per day of lactoferrin is probably biosynthesized, taking into consideration the biological half-life of neutrophil.

Since lactoferrin has a wide distribution and is synthesized in large amounts in living bodies, its applications have been examined in various industries. There have been reported a preventive effect on microorganism infection at each individual animal level (Miyazaki et al. Chemotherapy 39: 829-835 (1991)), and besides, cancer-related effects, for example, an anticancer effect (Bezault et al. Cancer Res. 54: 2310-2312 (1994)), a carcinogenesis preventive effect (Sekine et al. Jpn. J. Cancer Res. 88: 523-526 (1997)), a metastasis preventive effect (Kuhara, Rinsho Meneki (Clinical Immunology) 34: 376-381 (2000)), and a metastasis inhibitive effect by inhibiting neovascularization (Shimamura et al., proceedings of the 60th annual meeting of the Japan Cancer Association (October, 2001)). Lactoferrin is supposed to have various functions since it has a wide distribution and is synthesized in large amounts in living bodies. And because it exists in the eyes, the mucous membrane of the oral cavity and the gastrointestinal tract, the nasal cavity, and the mucus covering the bronchiole, through which living bodies are directly in contact with the outside world, there has been an emphasis particularly on its function as a first defensive wall for defending living bodies against infections of pathogenic microorganisms and viruses. And in recent years, lactoferrin has been used in clinical applications, for example, in the field of treatment for hepatitis C, secondary prevention of carcinoma of the colon and rectum, and Trichophyton infection of skin. However, there has been no report on effective use of lactoferrin for improving pain and getting rid of anxiety of patients suffering from pain. There has been known no example of trying treatment for rheumatoid arthritis, osteoarthritis, frozen shoulder, chronic low back pain, tennis elbow and baseball shoulder by orally administering lactoferrin to patients.

DISCLOSURE OF THE INVENTION

The inventors of this invention have conducted an extensive study of the effects of lactoferrin for many years.

In toxicity studies in beagles and rats carried out by the inventors in accordance with GLP, lactoferrin extracted from milk (manufactured by Tatua Milk Industry Co., Ltd., New Zealand, purity: 87%) was non-toxic after oral administration at physical limit doses. In single dose acute toxicity studies, no abnormal findings were observed in any animals even at the maximum dose of 5 g/kg. In subacute toxicity studies with a dosing period of 3 months, no abnormal findings were observed, either, in both kinds of animals at the maximum dose of 2 g/kg. Accordingly, lactoferrin is probably non-toxic after oral administration and has almost ideal characteristics as a therapy for cancer. It is likely that lactoferrin defends opportunistic infections frequently occurring in immunocompromised hosts such as patients with cancer, prevents carcinogenesis, inhibits the growth of cancer, prevents metastasis, and destructs a metastatic lesion. Further, it is probably highly safe when administered to patients declining in immunopotency, such as aged patients.

Thus, the inventors prepared enteric coated tablets of lactoferrin having been extracted from milk, asked volunteers with end-stage cancer to take the tablets, and summed up the results. From the results, were observed such effects that the patients having taken the lactoferrin-containing enteric coated tablets were all set free from severe pain and gotten rid of anxiety, and therefore had a better appetite (see Japanese Patent Application No. 2000-357573).

The inventors carried out, using rodent animals, animal tests related to pain: (1) hot plate test, (2) formalin test and (3) acetic acid rising test to examine the influences of lactoferrin administration on the animals' sensation of pain. As a result, they found that in any tests, administration of lactoferrin before test allowed the animals to have a weakened sensation of pain against the stimulation, in other words, lactoferrin was effective in alleviating pain. Further, the inventors compared the analgesic effect of lactoferrin with that of diclofenac, a typical non-steroidal antiinflammatory drug, and found that lactoferrin dose-dependently exhibited analgesic effect against the phase 1 pain, while diclofenac did not and that lactoferrin was superior to diclofenac even in analgesic effect against the phase 2 pain in terms of inhibiting strength and prolonged action (see examples 1 to 3 herein described).

The fact indicating that bovine lactoferrin administered to fish alleviates stresses in the fish has been already reported by Tsunoda (Tsunoda, Exc. Med. Int. Congr. Ser. 1195: 429-441, 2000). And the inventors of this invention examined in more detail whether or not lactoferrin exhibited an anti-stress effect even in mammals. As a result, they found that the administration of lactoferrin alleviated stresses in rats and reduced the onset of gastric ulcer in the same (see Example 4 herein described).

Further, the inventors administered orally enteric coated tablets of lactoferrin to patients with arthritis, frozen shoulder, low back pain, tennis elbow and baseball shoulder and found that the lactoferrin-containing tablets significantly improved the pain in the joints without causing any side effects (see examples 9 to 11).

Further, the inventors evaluated the effect of the oral administration of lactoferrin on joint pain in such a manner as to use adjuvant arthritis in rats as an experimental animal model, flex 10 times the adjuvant-injected foot, in which the toe joint had been swollen, of each rat's hind legs, and record the number of times each rat screamed out in pain. Normal rats do not scream even if their joints of hind legs are flexed because they do not have pain in the joints, but on the other hand, after onset of adjuvant arthritis, they respond sharply to the stimulation of their pain sensation. After lactoferrin administration to the rats with adjuvant arthritis, the number of time the rats screamed was significantly decreased even when their swollen joints were flexed. This indicated that lactoferrin was effective in weakening the pain sensation even in portion affected with arthritis (see examples 5 to 7 herein described). The lactoferrin's effect of weakening the pain sensation in arthritis-diseased portion is a novel discovery which enables lactoferrin to have wide applications in a variety of fields.

The examination by the inventors revealed that orally administered lactoferrin improved the disease of arthritis by the analgesic mechanism via the opioid system, and besides, produced preventive and therapeutic effects against inflammation by inhibiting the activity of the immune system (see Example 8). The examination by the inventors also revealed that lactoferrin had analgesic effect similar to that of morphine, and moreover, had the effect of enhancing the analgesic effect of morphine (see examples 12 and 13 herein described).

The inventors have accomplished this invention based on the above described novel and beneficial findings. Thus, this invention provides a novel analgesic containing lactoferrin as an active ingredient.

DETAILED DESCRIPTION OF THE INVENTION

Figure 1:
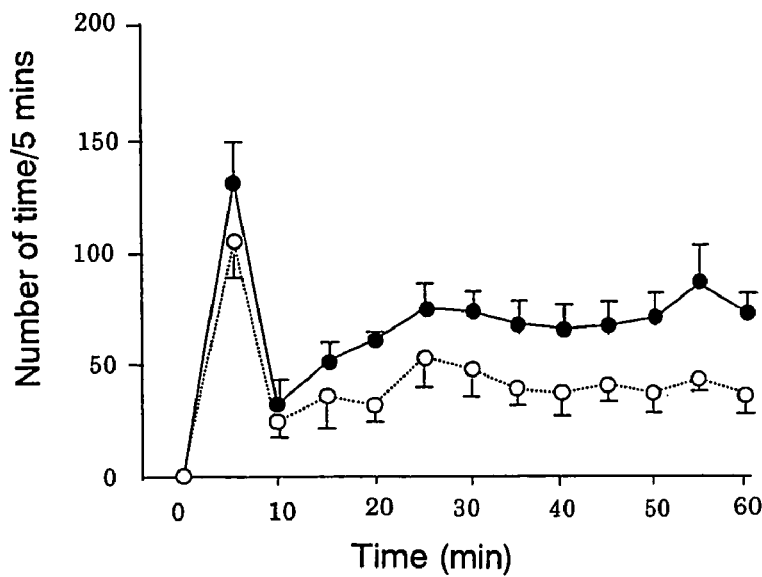
FIG. 1 is a graph showing the decrease in number of times rats lifted their feet after administration of lactoferrin (Example 1), the number of times being represent by the mean value for 5 rats per group + or − standard error, ● representing a control group, ○ representing a lactoferrin-administered group.

The novel analgesic of this invention is a composition containing lactoferrin as an active ingredient. Any type of lactoferrin can be used for the composition of this invention as long as it provides the effect discovered by the inventors of this invention when administered orally. Lactoferrin is a macromolecule having a molecular weight of about 80000 and has the property of forming a chelate with two trivalent iron ions. The term "lactoferrin" herein used includes any types of lactoferrin: those in an iron-free form and in an iron-saturated form; and those of any origin, for example, human, bovine and recombinants. Not only lactoferrin itself, but lactoferrin-like substances (e.g. proteins of the lactoferrin group or the enzymatic decomposition products of proteins of the lactoferrin group) may also be used for the composition of this invention. These compositions are also included within the scope of this invention. The "proteins of the lactoferrin group" include lactoferrin and conalbumin and the "enzymatic decomposition products of proteins of the lactoferrin group" include peptides corresponding to lactoferricin. The composition of this invention may contain only one kind of lactoferrin (or a protein of the lactoferrin group or the enzymatic decomposition product of a protein of the lactoferrin group) or two or more kinds.

The composition of this invention can be used for practical applications in dosage forms such as oral formulation, injectable formulation, suppository, poultice, formulation for drip infusion, gargle and lozenge. Particularly suitable form for practical applications is an oral formulation such as powdered drug, powder, granule, tablet, capsule, pill or solution, or an injectable formulation. The composition of this invention may take the form of a food, a drink or a health drink. The composition of this invention may also be administered in the form of an additive for food or feed.

Excipients used when the composition of this invention is made into a dosage form include: for example, monosaccharides or disaccharides such as lactose, sucrose and glucose; starches such as corn starch and potato starch; crystalline cellulose; and inorganic substances such as light silica gel, synthetic aluminum silicate, magnesium aluminate metasilicate and calcium hydrogenphosphate. Binders used include: for example, starches, carboxymethylcellulose (CMC), hydroxypropylcellulose (HPC), carboxymethylcellulose sodium salt and polyvinylpyrrolidone. Disintegrating agents used to disintegrate the dosage form to original primary particles in the lower gastrointestinal tract include: for example, starches, carboxymethylcellulose sodium salt, carboxymethylcellulose calcium salt, crosscarmelose sodium and carboxymethyl starch sodium. Film forming agents for coating tablets or granules to make them enteric-coated include: for example, hydroxypropylmethylcellulose phthalate, carboxymethylethylcellulose, acetate phthalate cellulose and methacrylic acid copolymer, all of which dissolve at pH 5 to 6; and shellac which dissolves in the alkaline region.

Preferably the composition of this invention is made into a dosage form while being kept in the dried state. The reason is that lactoferrin as an active ingredient of the composition of this invention is unstable under the circumstances of high temperature and humidity. In particular, an amino-carbonyl reaction may occur between an amino group of lactoferrin and a reductive group existing in the excipients, etc. This results in the formation of brown coloring matter due to the polymerization of the reactants by an irreversible process through a plurality of steps (browning reaction). The existence of substances that catalyze oxidation and high temperatures accelerate this reaction. Specifically, when lactoferrin is made into a dosage form, if water exists, amino-carbonyl reaction may be accelerated because of the effect of $Fe^{3+}$, etc. contained in lactoferrin. And an exothermic reaction due to tablet compression also accelerates this reaction. Thus, to obtain a stable lactoferrin formulation in which the pharmacological action is maintained, it is preferable to make the composition into a dosage form while keeping the composition in the dried state as much as possible.

Lactoferrin cannot undergo tablet compression as it is, because it generally has a very low specific gravity. Accordingly, to allow the composition of this invention to take a stable tablet form in which the pharmacological action is maintained, the steps are taken of: for example, mixing the active ingredient with an excipient, a binder and a disintegrating agent; slug-compacting the mixture with a slugging machine to form a large thin flat disk; crushing the disk; and sieving the crushed disk to obtain granules of a uniform size. When intending to make the granules into a tablet, the granules are tablet-compressed after adding lubricant thereto, and if desired, the tablet is coated with a coating film to yield a product. When intending to make the granules into a capsule, a prescribed amount of the granules are packed into a capsule.

Preferably the composition of this invention, as a composition for an oral formulation, is made into an enteric-coated dosage form. The inventors of this invention hypothesize that there exists a structure, which can be referred to as a lactoferrin sensor, on the mucosa of the intestinal tract, as described in detail in International Patent Application, PCT/JP01/10212 (WO02/41912). And at the same time, they have found that lactoferrin is highly sensitive to pepsin, but significantly resistive to protease. Specifically, in the composition containing lactoferrin, which acts on the mucosa of the intestinal tract and is highly sensitive to pepsin, it is technologically meaningful to make the composition into an enteric-coated dosage form.

To make the composition into an enteric-coated dosage form, it is preferable to pack the granules containing the active ingredient into an enteric-coated capsule of a film whose main ingredient is a base, which is resistant to gastric juice and dissolved in the small intestine, selected from the group consisting of, for example, shellac, Tween, hydroxypropylmethylcellulose phthalate, carboxymethylethylcellulose, acetate phthalate cellulose, methacrylic copolymer, water-insoluble ethylcellulose and aminoalkylmethacrylate copolymer, or to coat the tablet, which is obtained by adding lubricant to the granules containing the active ingredient and tablet-compressing the same, with the above film.

The inventors of this invention confirmed that there existed lactoferrin in the blood of the patients who had orally taken the enteric coated tablets of lactoferrin. This finding has not been obtained from the existing lactoferrin formulations. The lactoferrin-containing composition in the enteric-coated dosage form is one of the preferred embodiments of this invention. Further, the lactoferrin-containing composition in the enteric-coated dosage form which has been made into the dosage form while being kept in the dried state is one of the particularly preferred embodiments of this invention.

Whether the produced composition is enteric-coated or not can be confirmed by conducting a disintegration test using: a first fluid which is obtained by dissolving 2.0 g of sodium chloride in 24 ml of dilute hydrochloric acid and water to make 1000 ml (pH: 1.2, Japanese Pharmacopoeia, General Tests 41); and a second fluid which is obtained by adding 118 ml of 0.2 N sodium hydroxide TS and water to 250 ml of 0.2 M potassium dihydrogenphosphate TS to make 1000 ml (pH: 6.8). Tablets or granules that do not disintegrate when immersed in the first fluid for 120 minutes, but do disintegrate when immersed in the second fluid for 60 minutes are not dissolved in the stomach, but disintegrated first when flowing into the duodenum, where their active ingredients are eluted. Such tablets or granules are judged to be enteric-coated.

The composition of this invention is beneficial to treating at least one disease or condition selected from the group consisting of pains, including the phase 1 pain and the phase 2 pain, anxiety and stress. The composition is particularly beneficial to alleviating or subsiding the pain and anxiety which may significantly lower the quality of life of patients with end-stage cancer. The composition is also beneficial to treating pains, including the phase 1 pain and the phase 2 pain, which accompany arthritis and diseases in the junctions of bones and inflammation. Arthritis and diseases in the junctions of bones include, for example, rheumatoid arthritis, osteoarthritis, frozen shoulder, sports injuries such as tennis elbow and baseball shoulder, and low back pain. The term "treatment" herein used means preventing, curing or subsiding, and alleviating diseases or conditions as the objects of treatment, unless otherwise specified. The term "the phase 1 pain" herein used means a localized sever penetrating pain, unless otherwise specified. And the term "the phase 2 pain" herein used means a burning pain occurring late and lasting long.

The composition of this invention can be combined with other drugs: for example, analgesics (narcotic analgesics such as morphine, codeine, dihydrocodeine, ethylmorphine and oxycodon); and antiinflammatory drugs/antiallergics (e.g. non-steroidal antiinflammatory drugs, steroidal antiinflammatory drugs and antiphlogistic). The composition can also enhance the effect of the drugs co-administered. In particular, the use of the composition in combination with morphine enables the dosage of morphine to be significantly decreased.

Lactoferrin, the active ingredient of the composition of this invention, can increase bifidobacteria and lactic acid bacteria in the lower gastrointestinal tract, and therefore its administration does not cause side effects such as flatus, diarrhea and feeling of distension.

The composition of this invention can be administered to patients who need the treatment with the composition of this invention in a daily dose of, in terms of the active ingredient, about 0.1 mg to about 50,000 mg, preferably about 0.5 mg to about 10,000 mg, and most preferably about 10 mg to about 2,000 mg at a time or in divided portions before meals, after meals, between meals and/or before going to bed. The dose can be determined depending on the age and weight of patients and the objective of the administration, individually.

The analgesic effect of lactoferrin as the active ingredient of the composition of this invention disappears when administered concurrently with naloxone. Naloxone is known to be antagonistic to morphine and make the analgesic effect of morphine to be ineffective. This indicates that the mechanism of the analgesic effect of lactoferrin is possibly similar to that of morphine. In other wards, lactoferrin possibly acts on a μ-opioid receptor as a center of transferring pain sensation stimulation and blocks the transfer, like morphine. However, lactoferrin is not addictive, unlike morphine. And besides, in the examination of the inventors, symptoms such as poor appetite and weight loss, which are side effects of opioid, were not observed in the lactoferrin-administered animals and their general conditions were good. Thus, it is clear that the mechanism of lactoferrin's blocking the transfer of pain sensation stimulation is not the same as that of morphine. Then the inventors focused on the fact that the cytokine concentration in the blood plasma is increased in rats affected with adjuvant arthritis, and examined in detail the influence of the oral administration of lactoferrin on the production of cytokine. In the examination, the level of tumor necrosis factor (TNF-α), as a marker of inflammation, significantly decreased, while that of interleukin-10 (IL-10), as an antiinflammatory cytokine, significantly increased. This reveals that the oral administration of lactoferrin activates the immune system and acts to allow inflammation to subside. The characteristic of lactoferrin such that it acts to decrease the TNF-α level while increasing IL-10 is ideal for treatment of arthritis.

It has been proved that, when orally administered, lactoferrin, the active ingredient of the composition of this invention, not only improves the diseases of arthritis by its analgesic mechanism via the opioid system, but also provides preventive and therapeutic effects against inflammation by inhibiting the activations of the immune system. Alleviation of pain associated with arthritis is an important clinical target, and the fact that lactoferrin has both analgesic and antiinflammatory effects means lactoferrin is very beneficial as the active ingredient of a novel oral formulation for treatment of arthritis.

The invention will be described below in more detail taking several examples; however, it should be understood that these examples are not intended to limit the invention.

EXAMPLES

Production Example 1

Twenty five g of purified dextrose was added to 0.5 g of human lactoferrin (purity: 98% or more) produced by black koji-mold into which the human lactoferrin gene had been introduced by recombinant DNA technique, and the mixture was dissolved in 5 ml of purified water and filter sterilized. The filtrate was put into a vial and freeze-dried to produce lactoferrin powder for injection.

Production Example 2

Tablets 8 mm in diameter and 180 mg in weight each containing 50 mg of lactoferrin were introduced into a coater and sprayed with an enteric coating liquid consisting of 9% of carboxymethylcellulose, 1% of glycelol fatty acid ester, 45% of ethanol and 45% of methylene chloride to apply the coating to the tablets to produce enteric coated tablets with a coating to tablet weight ratio of 12%.

Production Example 3

One kg of lactoferrin extracted from bovine milk and 0.9 kg of arabic gum powder were mixed and the mixture was granulated with a dry granulating machine. The granules were mixed with 60 g of powdery cured vegetable oil and compressed with a flat punch 10 mm in diameter into tablets, as oral cavity attaching tablets, each weighing 100 mg.

Production Example 4

Production of Enteric Coated Tablet of Lactoferrin 5.5 kg of lactoferrin, 8 kg of lactose, 10 kg of crystalline cellulose, 1 kg of carboxymethylcellulose calcium and 0.5 kg of glycerol fatty acid ester were mixed and dry granulated in the same manner as in Example 1. The granules were pressed into tablets 8 mm in diameter and 250 mg in average weight, each containing 50 mg of lactoferrin. The tablets were introduced into a coater (manufactured by Freund Corporation, High Coater HCT-48N) and sprayed with a calculated amount of a liquid prepared by dissolving 30 parts of shellac and 7 parts of castor oil in 63 parts of isopropanol to produce enteric coated tablets with a coating to tablet weight ratio of 10%.

Example 1

Formalin Test (Acute Toxicity Study)

Formalin test is a typical pain sensation stimulating test. It is a method for determining an analgesic effect of drugs in which 50 μl of 2% formalin is injected into a foot pad of each experimental rat and the foot-lifting and foot-licking behavior of the rats is observed.

Ten male Wistar rats (6 weeks of age) were randomly divided into two groups, and one hour before injecting formalin, the rats in the control group were given saline solution (1 ml/kg) and those in the lactoferrin group were given bovine lactoferrin dissolved in saline solution (100 ml/kg, Tatua Milk Industry Co., Ltd., purity: 87%) by intraperitoneal injection. After one hour, formalin solution was injected into the foot pad of each rat, and the foot-lifting and foot-licking behavior of each rat due to the stimulation of the pain sensation was measured for one hour (FIGS. 1 and 2).

As is apparent from FIG. 1, following intraperitoneal administration of lactoferrin one hour before formalin stimulation, the foot-lifting behavior of the rats significantly decreased. Analysis of variance showed that there was significant difference between the two groups at a significance level of P<0.0001 or less. When lactoferrin was administered at higher doses, the foot-licking behavior of the rats significantly decreased (data not shown).

Figure 2:
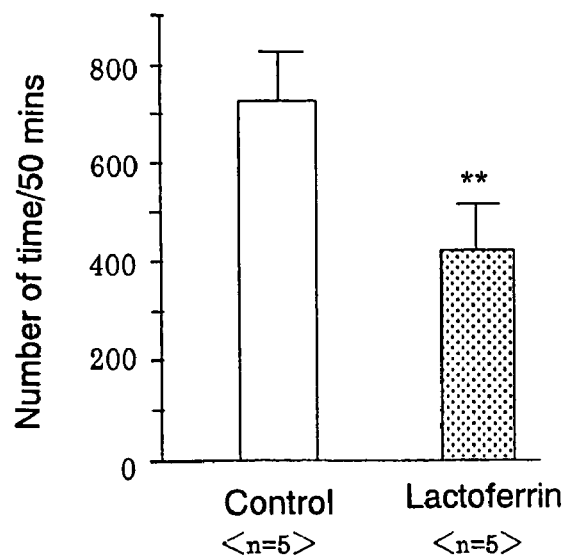
FIG. 2 is a graph showing the number of times rats lifted their feet due to the phase 2 pain stimulation within 50 minutes after injection of formalin (Example 1), **$P<0.01$ (Student's t-test), bar representing mean+SE.

As shown in FIG. 2, the number of time the rats lifted their feet within 50 minutes after formalin injection (due to the phase 2 pain sensation stimulation (a severe penetrating pain occurring late) by formalin) more significantly decreased in the lactoferrin group than in the control group. This indicated that the sensitivity to pain was more weakened in the rats in the lactoferrin group than those in the control group.

Example 2

Formalin Test (Subacute Toxicity Study)

In Example 1, the effect of lactoferrin on the pain sensation when administered by intraperitoneal administration was studied. In this example, the effect of lactoferrin on the pain sensation when administered orally was studied.

Fourteen male Wistar rats (6 weeks of age) were randomly divided into two groups, and the rats in one group were fed standard feed powder for rodent animals (Clea Japan, Inc., CE-2) while those in the other group fed CE-2 with 1% bovine lactoferrin added thereto for 4 weeks. Four weeks later, formalin solution was injected into the foot pad of each rat, and the foot-lifting and foot-licking behavior of each rat due to the pain sensation stimulation was measured for one hour (FIGS. 3 and 4).

Figure 3:
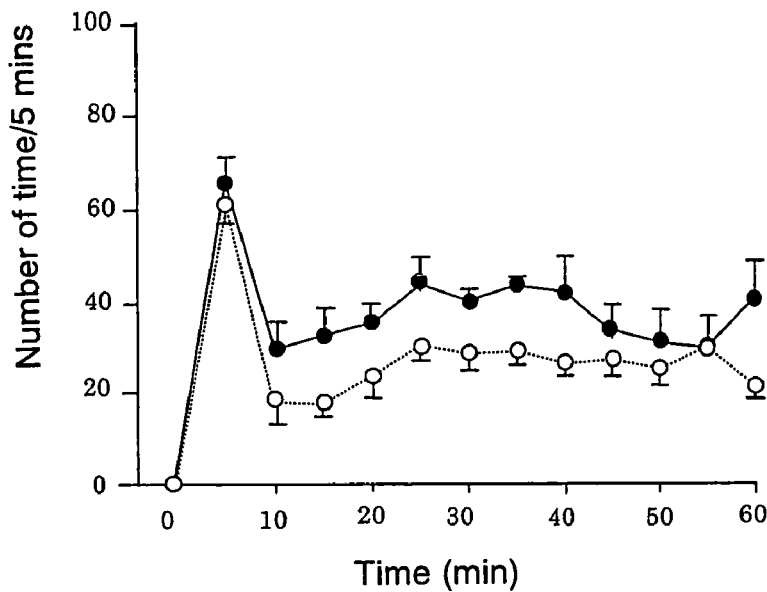
FIG. 3 is a graph showing the decrease in number of times rats lifted their feet after oral administration of lactoferrin (Example 2), the number of times being represent by the mean value for 7 rats per group + or − standard error, ● representing a control group, ○ representing a lactoferrin-administered group.

As is apparent from FIG. 3, even when orally administered, lactoferrin functioned so that it alleviated the stimulation of the pain sensation in the rats, in other words, weakened the sensitivity to pain in rats. Analysis of variance showed that there was significant difference between the two groups at a significance level of P<0.0001 or less. The analysis also confirmed that the foot-licking behavior of the rats significantly decreased.

Figure 4:
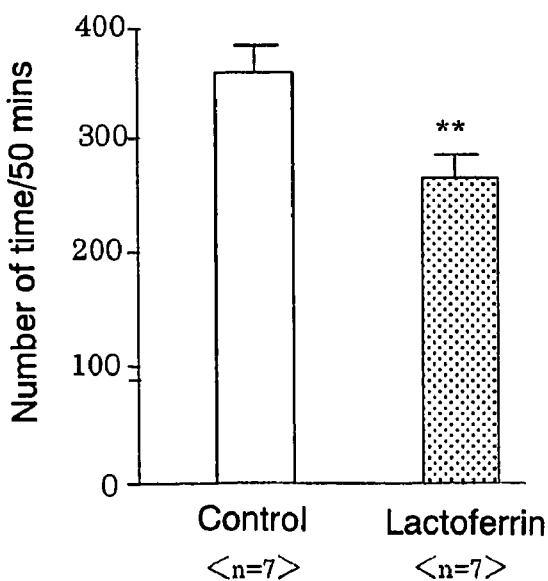
FIG. 4 is a graph showing the number of times rats lifted their feet due to the phase 2 pain stimulation within 50 minutes after injection of formalin (Example 2), **$P<0.01$ (Student's t-test), bar representing mean+SE.

As is apparent from FIG. 4, even when orally administered, lactoferrin provided the effect of significantly inhibiting the phase 2 pain sensation stimulation (a severe penetrating pain occurring late) induced by formalin.

Example 3

Comparison with Non-Steroidal Antiinflammatory Drug

The analgesic effect of lactoferrin was compared with that of diclofenac, a typical non-steroidal antiinflammatory drug.

Male Wistar rats 6 weeks of age were used. The rats in one group were given bovine lactoferrin and those in another group were given a control drug, diclofenac, by intraperitoneal administration 30 minutes before injecting formalin into their foot pads. Their responses to pain are shown in FIG. 5: the phase 1 pain (left) and the phase 2 pain (right).

Figure 5:
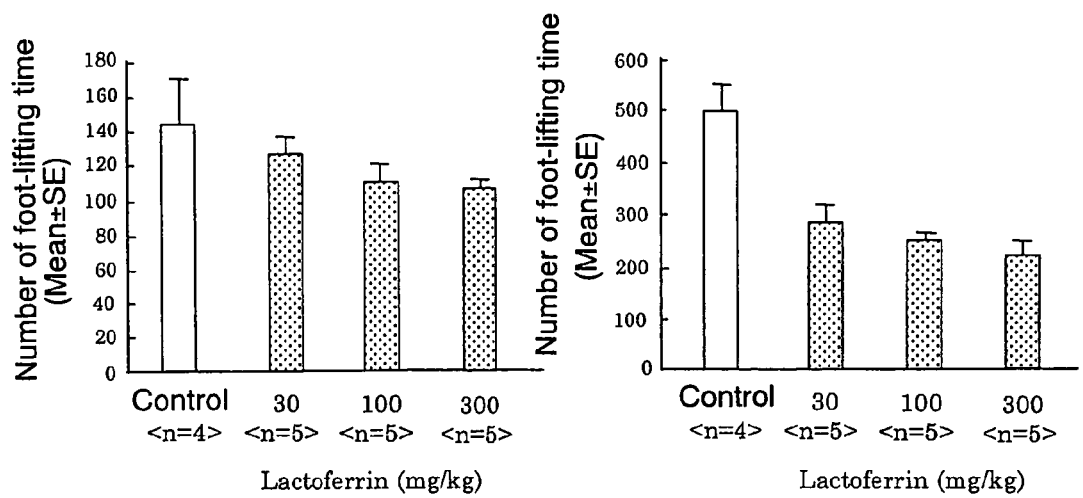
FIG. 5 is graphs showing the number of times rats lifted their feet within 50 minutes after injection of formalin (Example 3), the left showing the number resulted from the phase 1 pain stimulation, the right showing the number resulted from the phase 2 pain stimulation.
Figure 6:
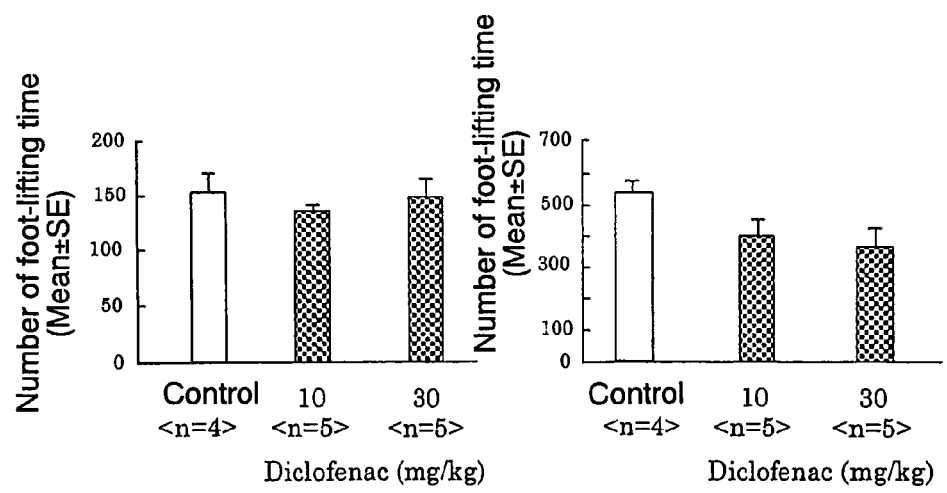
FIG. 6 is graphs showing the number of times rats lifted their feet within 50 minutes after injection of formalin (Example 3), the left showing the number resulted from the phase 1 pain stimulation, the right showing the number resulted from the phase 2 pain stimulation.

As is apparent from FIG. 5, lactoferrin inhibited dose-dependently both the phase 1 pain and the phase 2 pain. On the other hand, diclofenac inhibited the phase 2 pain, but the degree of inhibition was low compared with that by lactoferrin. In other words, lactoferrin was found to have the effect of inhibiting both "a localized sever penetrating pain" and "a burning pain occurring late and lasting long".

Figure 7:
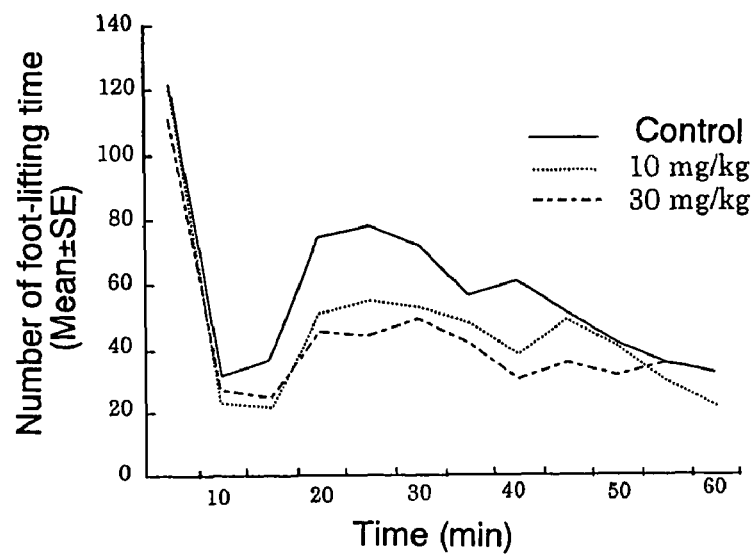
FIG. 7 is a graph showing the pain inhibiting effect of diclofenac (Example 3)
Figure 8:
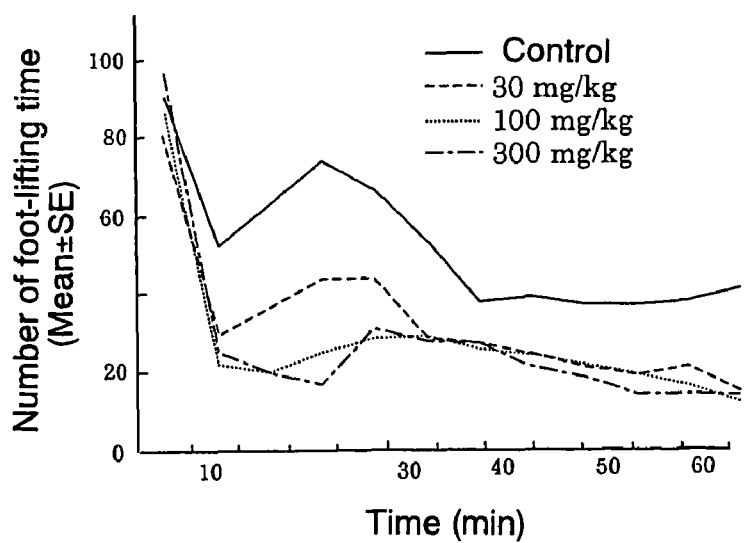
FIG. 8 is a graph showing the pain inhibiting effect of lactoferrin (Example 3)

The measurements of pain inhibiting effects of both lactoferrin and diclofenac with time are shown in FIGS. 7 and 8. Lactoferrin and diclofenac were administered intraperitoneally 30 minutes before formalin injection both in the control group (n=4) and the diclofenac group (n=5). The pain inhibiting effect of diclofenac disappeared about 50 minutes after formalin injection, whereas the pain inhibiting effect of lactoferrin lasted long and even 60 minutes after formalin injection. Significantly high inhibiting effect was observed. The results showed that lactoferrin had not only an anesthetic effect against localized pain, but also inhibiting effect against a long-lasting burning pain, which patients with end-stage cancer complain of.

Example 4

Effect Against Stress

Sixteen male Wistar rats (6 weeks of age) were randomly divided into two groups, and the rats in one group (n=8) were fed standard feed powder for rodent animals (CLEA JAPAN, INC., CE-2) while those in the other group (n=8) fed CE-2 with 1% bovine lactoferrin added thereto for 8 weeks. Eight weeks later, the rats were deprived of food for one night, administered orally and forcibly 5 ml/kg weight of 50% ethanol, and subsequently inflicted with restriction stress for 2 hours. Two 2 hours later, the stomach of each rat was excised and "number of hemorrhagic spots", "area of hemorrhage", "number of ulcers", "number of large ulcers" and "areas of ulcers" on the gastric mucosa were measured.

Administration of lactoferrin decreased the number, per rat, of the hemorrhagic spots on the gastric mucosa to 87%. The area of the hemorrhage per rat also decreased to 79% in the lactoferrin-administered group. The number of the ulcers and the number of the large ulcers also decreased to 50% in the lactoferrin-administered group and the area of the ulcers decreased to about 30%. This indicates that lactoferrin prevented the formation of gastric ulcer. The experiment results show that lactoferrin has a stress inhibiting effect.

Example 5

Prevention of Arthritis

The preventive/therapeutic effects against arthritis of orally administered lactoferrin (LF) and the mechanism of the action were examined using an adjuvant arthritis rat model as an animal model with rheumatoid arthritis.

Evaluation of the above described effects was performed by measuring the change in volume of foot due to swelling, Flexion test (pain in joints caused in flexion and extension test), and the production of cytokine by the stimulation of lipopolysaccharide.

Adjuvant was injected subcutaneously into the sole of the right hind leg of each rat, and the volume of the feet was measured once a day to obtain the swelling rate of the feet of both hind legs. The test substance was suspended in 0.5% CMC and administered once or twice a day for 18 consecutive days starting from the first dose 3 hours before adjuvant treatment (day 0). On 4th and 10th days after treating with adjuvant, the swollen tarsal joint of each rat was extended 10 times and the number of times each rat screamed due to the stimulation of pain sensation caused by flexing and extending its tarsal joint was measured.

Figure 9:
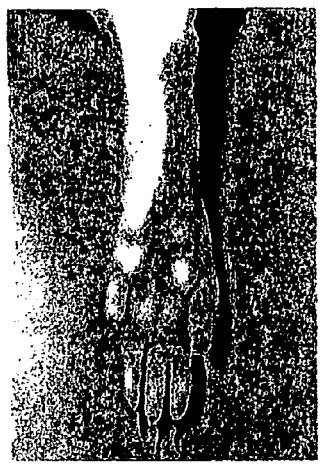
FIG. 9 is photographs of hide legs of rats (Example 5), the upper column showing the hide legs of a normal rat, the middle a rat, the lower an adjuvant-treated rat orally administered lactoferrin, -1 representing the treated leg while -2 representing the other leg in each column.
Figure 9:
Figure 9:
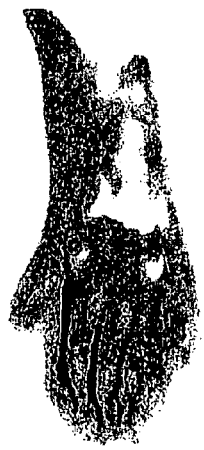
Figure 9:
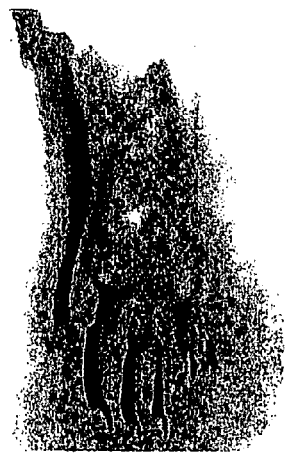
Figure 9:
Figure 9:
Figure 10:
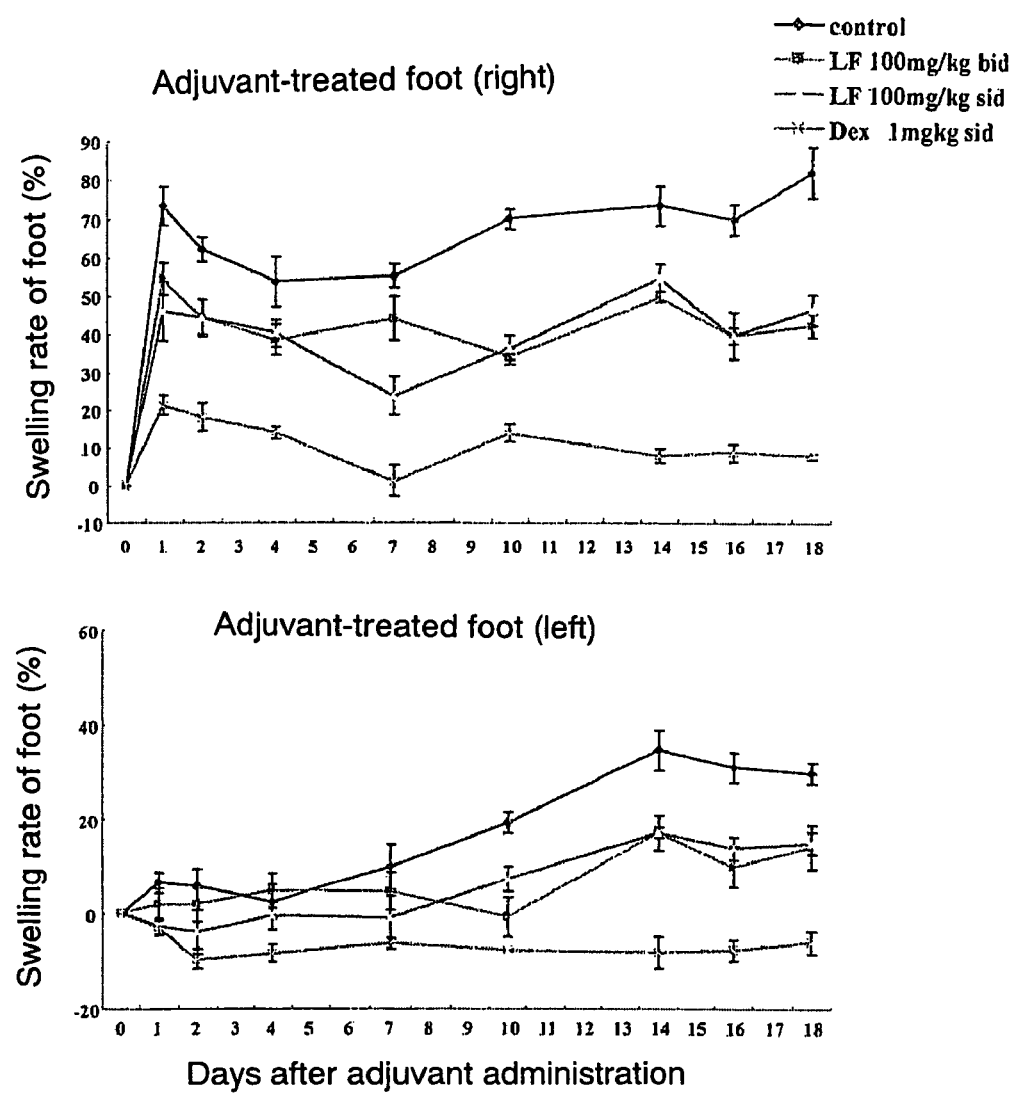
FIG. 10 is graphs showing the swelling rate (%) of adjuvant-treated feet and adjuvant-untreated feet, respectively (Example 5)
Figure 11:
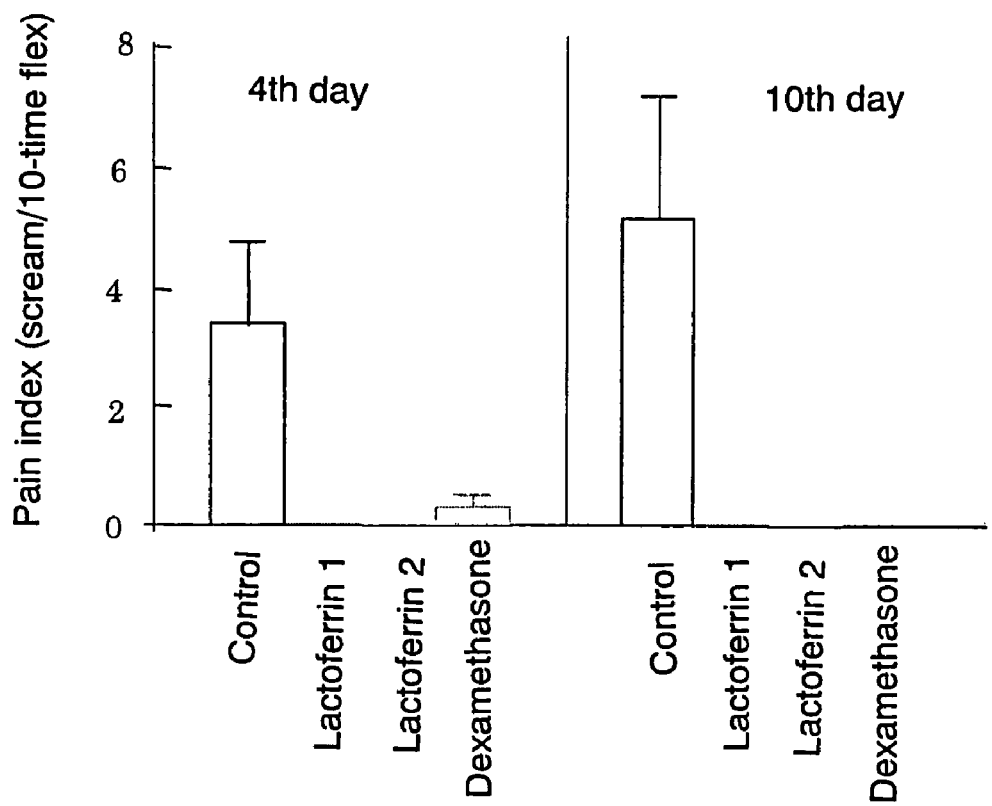
FIG. 11 is a graph showing the results of Flexion tests (Example 5)

FIG. 9 shows photographs of the hide legs of a normal rat orally administered 0.2 ml of 0.5% CMC aqueous solution (upper column), an adjuvant-treated rat orally administered 0.2 ml of 0.5% CMC aqueous solution (middle column) and an adjuvant-treated rat orally administered 100 mg/kg of lactoferrin (lower column), -1 representing the adjuvant-treated leg while -2 representing the other leg in each column. FIG. 10 shows the swelling rate (%) of adjuvant-treated feet and adjuvant-untreated feet in the control group, in the group orally administered 100 mg/kg of LF once daily (100 mg/kg sid) or twice a day (100 mg/kg bid), and in the group intraperitoneally administered 1 mg/kg of dexamethasone once daily (Dex 1 mg/kg sid), respectively. FIG. 11 shows the results of Flexion tests.

As shown in FIG. 10, the swelling rate of the feet was significantly lower in the lactoferrin administered groups than in the control group throughout the period, from the period of the acute phase to that of the chronic phase of inflammation, after adjuvant treatment. As shown in FIG. 11, the rats of the groups orally administered lactoferrin, including both the groups administered once a day and twice a day, neither screamed nor showed pain sensation reaction. In the dexamethasone administered group as a positive control, some rats screamed in pain on day 4.

The swelling rate of the feet was lower in the dexamethasone administered group, a positive control, than in the lactoferrin administered groups, whereas the pain index in Flexion test was a little higher in the dexamethasone administered group than in the lactoferrin administered groups. In the dexamethasone administered group, sever inhibition of weight gain was observed and the conditions of the animals such as luster of fur were not good, but on the other hand, in the lactoferrin administered groups, weight gain was similar to that in the control group and the general conditions of the animals were good.

Example 6

Treatment of Arthritis

Figure 12A:
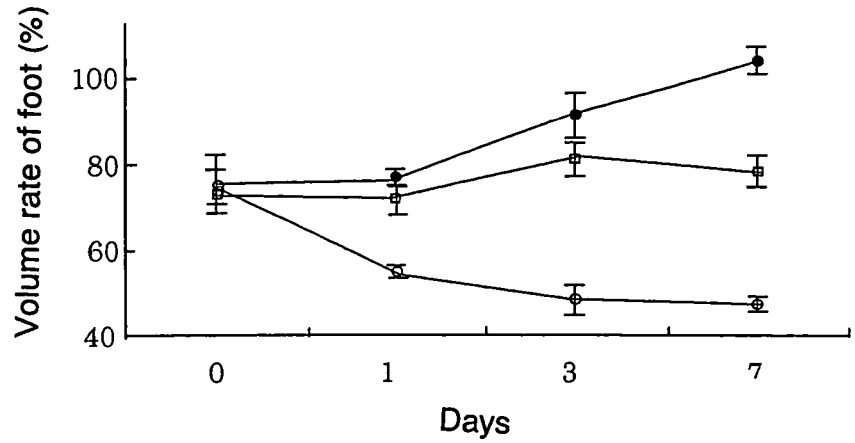
FIGS. 12A to 12C are graphs showing the therapeutic effect of lactoferrin in rats with adjuvant arthritis (Example 6): the volume ratio of the adjuvant-treated feet, the volume ratio of the adjuvant-untreated feet and the results of Flexion test in alphabetical order, ● representing a control group, □ a lactoferrin-administered group, ○ a dexamethasone-administered group.
Figure 12B:
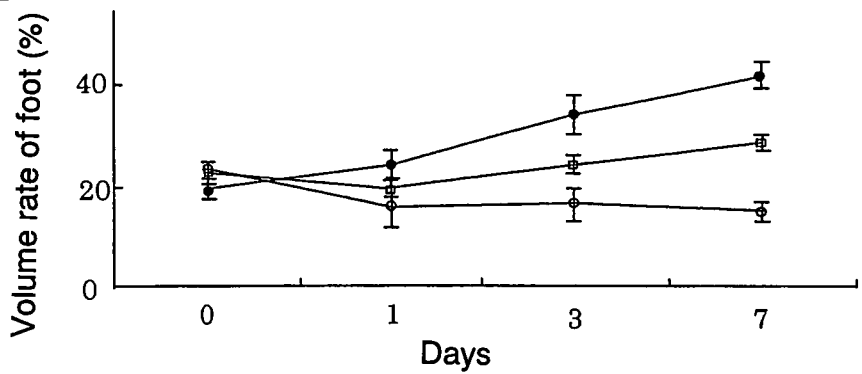
Figure 12C:
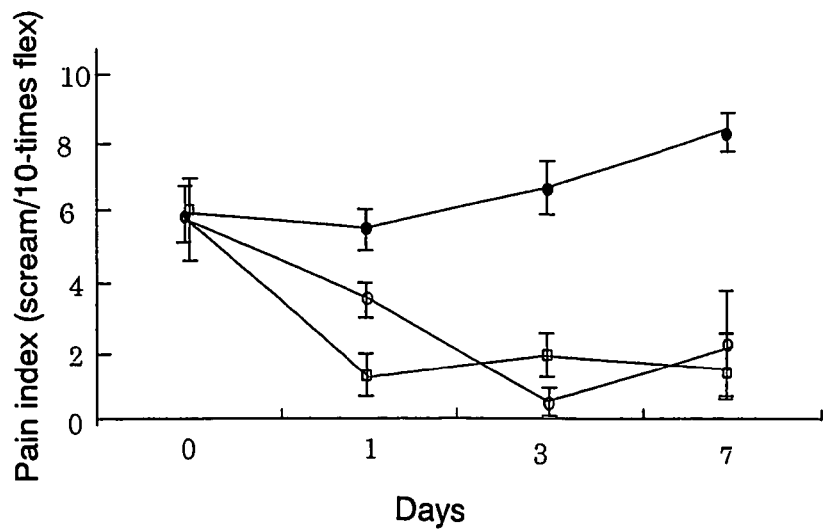

Subsequently after Example 5, lactoferrin (100 mg/kg) was orally administered for 7 consecutive days starting from day 19 after the adjuvant treatment, when the adjuvant treated rats were in the chronic phase of inflammation. The results are shown in FIGS. 12A to 12C.

On day 7 after the administration, the swelling rate of feet was significantly lower in the lactoferrin administered group than in the control group. And the pain index in Flexion test was also significantly lower in the lactoferrin administered groups than in the control group from day 1 to the day when the test was completed. In the dexamethasone (1 mg/kg) administered group, the swelling of the feet was obviously reduced from day 1 after the administration, but the pain index in Flextion test was a little higher than that of the lactoferrin administered groups. This indicates that the reducing effect of lactoferrin against the sensitivity to pain is almost the same as or higher than that of dexamethasone as shown in FIG. 12C.

Example 7

Improvement of Pain by Oral Administration of a Single Dose

Then, examined was whether or not oral administration of a single dose of lactoferrin could improve the pain in adjuvant arthritis models.

On day 25 after the adjuvant treatment, the rats were divided into 6 groups and administered once BSA (bovine serum albumin) or LF (lactoferrin), and after 3 hours, the pain index was measured for each group by Flexion test in the manner as in Example 5. Thirty minutes before Flexion test, saline solution, morphine or naloxone was administered subcutaneously.

Figure 13:
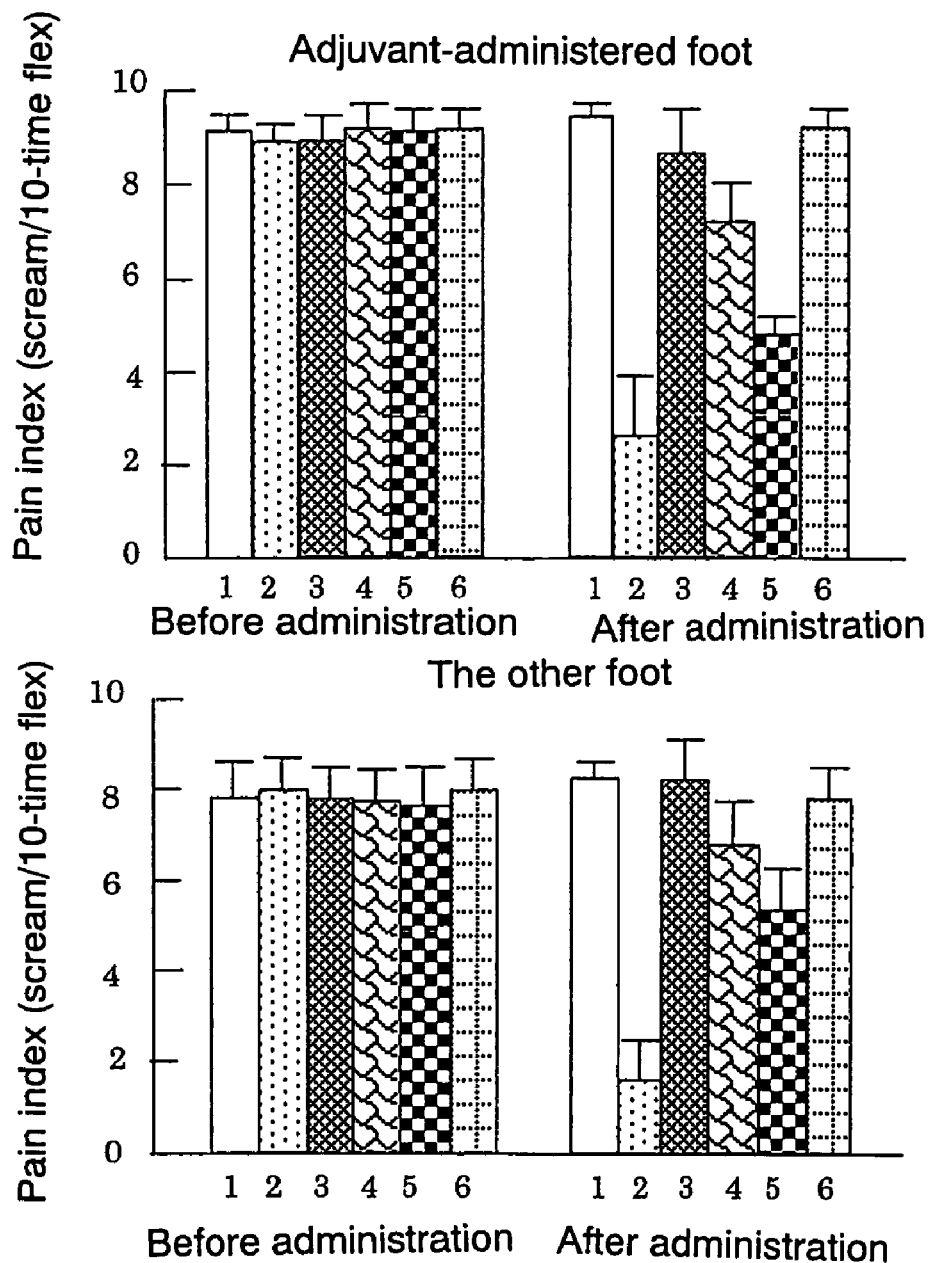
FIG. 13 is graphs showing the hyperalgesia inhibiting effect by a single dose of lactoferrin in the adjuvant-treated feet and the adjuvant-untreated feet, respectively (Example 7)

The design of the experiment is shown in Table 1 and the results in FIG. 13.

TABLE 1

Timing of drug administration in single dose experiment

| | Drug administration | |
| --- | --- | --- |
| Group | 3 hrs before Flexion test | 30 mins before Flexion test |
| 1 | BSA, 100 mg/kg | Saline solution |
| 2 | BSA, 100 mg/kg | Morphine, 3 mg/kg |
| 3 | BSA, 100 mg/kg | Naloxon, 3 mg/kg |
| 4 | LF, 10 mg/kg | Saline solution |
| 5 | LF, 100 mg/kg | Saline solution |
| 6 | LF, 100 mg/kg | Naloxon, 3 mg/kg |

As shown in FIG. 13, a single dose administration of lactoferrin at 10 to 100 mg/kg inhibited the sensitivity to pain in the joints dose-dependently. And the analgesic effect of lactoferrin was completely inhibited by naloxone.

Example 8

Mechanism of Action of Lactoferrin

It is known that in adjuvant arthritis models, the production of cytokines due to the LPS stimulation increases considerably, compared with normal animals, because the reactivity of their immune system increases due to chronic inflammation. To examine the mechanism of the action of lactoferrin against arthritis which has been proved herein so far, the effect of lactoferrin on the production of cytokines due to the LPS stimulation was examined in the group of rats administered lactoferrin for 19 consecutive days and in the group administered a single dose of lactoferrin.

Figure 14:
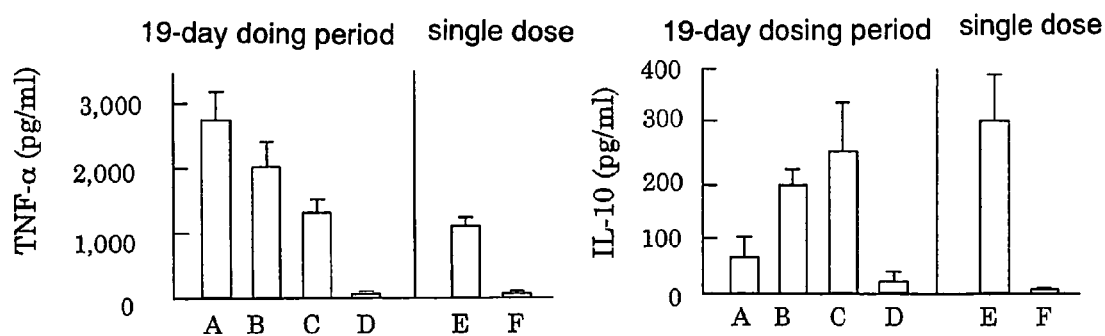
FIGS. 14 are graphs showing the cytokine-production inhibiting effect of lactoferrin (Example 8)

One mg/kg of LPS was administered intraperitoneally to rats with adjuvant arthritis to stimulate the production of cytokines. Three hours after the LPS administration, the blood was collected from each rat and the quantities of cytokines were measure by ELISA. The groups to be administered a single dose of lactoferrin (groups B and C) were given orally 0.5% CMC once daily until the experiment day to allow the experiment conditions to match those of the group to be administered lactoferrin for 19 consecutive days. The group to be administered lactoferrin for 19 consecutive days (group E) was administered orally lactoferrin once daily from the very day when treated with adjuvant. The design of the experiment is shown in Table 2 and the results in FIG. 14.

TABLE 2

Experimental conditions

| Group | Compound administered | Remarks |
| --- | --- | --- |
| A | 3% CMC solution | Untreated control |
| B | Lactoferrin 100 mg/kg | Last oral administration 3 hrs before blood collection |
| C | Lactoferrin 10 mg/kg | Last oral administration 3 hrs before blood collection |
| D | Dexamethasone 1 mg/kg | Last oral administration 30 mins before blood collection |
| E | Lactoferrin 100 mg/kg | Oral administration 3 hrs before blood collection |
| F | Dexamethasone 1 mg/kg | Intraperitoneal administration 30 mins before blood collection |

As a result, significant inhibition of TNF-α production and increase in IL-10 production were observed both in the group administered lactoferrin for 19 consecutive days and in the group administered a single dose of lactoferrin. In the dexamethasone administered group, decrease both in TNF-α production and in IL-10 production was observed.

Example 9

Osteoarthritis

Lactoferrin extracted from bovine milk was formed into enteric coated tablets (Production Example 4) and given orally to a 66-year-old man whose right knee and right elbow were affected by osteoarthritis associated with the injuries caused by his falling off a bicycle and a 61-year-old man whose knee joints were affected by osteoarthritis associated with obesity. Lactoferrin was administered at a dose of 150 mg (450 mg per day) 3 times a day after each meal. In the former and the latter cases, the patients had been treated with diclofenac and ibuprofen, respectively, but both of them failed to respond to the respective drugs. However, when administered the enteric coated tablets of lactoferrin, the former did not feel pain one week after the initial administration and the latter 2 months after the same, and thus they were cured of the disease.

Example 10

Effect Against Chronic Low Back Pain

A 55-year-old male volunteer and a 42-year-old female volunteer both suffering from low back pain took orally the enteric coated tablets of lactoferrin from bovine milk (Production Example 4). They took lactoferrin in a daily dose of 450 mg in 3 uniformly divided portions after each meal. Low back pain disappeared and was cured in the female volunteer on day 5 after the initial administration and in the male volunteer on day 12 after the same.

Example 11

Effect Against Frozen Shoulder

Three male volunteers 52, 45 and 48 years of age, each of who was affected frozen shoulder and could not raise either one of his hands above the shoulder, took orally the enteric coated tablets of lactoferrin from bovine milk (Production Example 4). In each case, the patient failed to respond to diclofenac. They took lactoferrin in a daily dose of 450 mg in 3 uniformly divided portions after each meal. Low back pain disappeared and was cured in one volunteer on day 7 after the initial administration and in the other volunteers on day 12 and on day 23 after the same, respectively.

Example 12

Comparison of Analgesic Effect with Morphine

The analgesic effects of bovine lactoferrin and recombinant human lactoferrin were compared with that of morphine.

Groups consisting of male Wistar rats 6 weeks of age (n=6 to 8) were intrathecally administered 0.1 to 100 μg/rat of bovine lactoferrin (bLF), 100 μg/rat of recombinant human lactoferrin (rhLF) or 10 μg/rat of morphine (Mor) 30 minutes before formalin was injected into their foot pads. The results are shown in FIGS. 15: the number of the foot-lifting times in the phase 1 pain (left graph) and the number of the foot-lifting times in the phase 2 pain (right graph).

Figure 15:
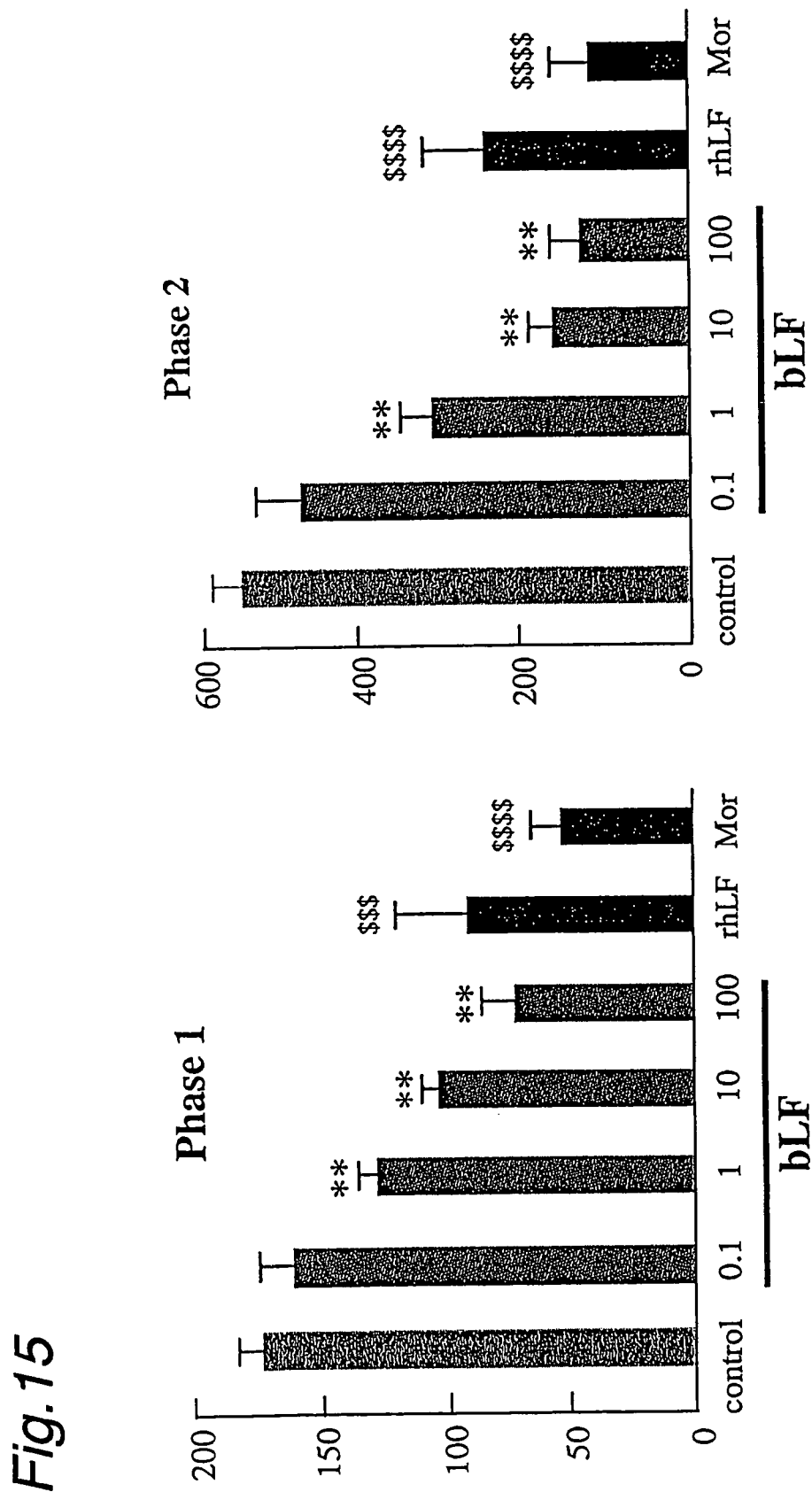
FIGS. 15 are graphs showing the pain inhibiting effect of lactoferrin administered intraspinally compared with that of morphine, $^{\$\$\$}P<0.005$, $^{\$\$\$\$}P<0.001$ (vs. control, Student's t-test), **$P<0.01$ (vs. control, Dunnett's test)

As is apparent from FIGS. 15, the intrathecal administration of lactoferrin inhibits both the first and the phase 2 pains, like morphine.

Example 13

Effect of Enhancing Analgesic Effect of Morphine

The lactoferrin's effect of enhancing the analgesic effect of morphine was examined by administering 1 to 10,000 ng/rat of morphine concurrently with 10 ng/rat of bovine lactoferrin (■) or alone (●) in the same manner as in Example 12. The results are shown in FIG. 16: the number of the foot-lifting times in the phase 1 pain (left graph) and the number of foot-lifting time in the phase 2 pain (right graph).

Figure 16:
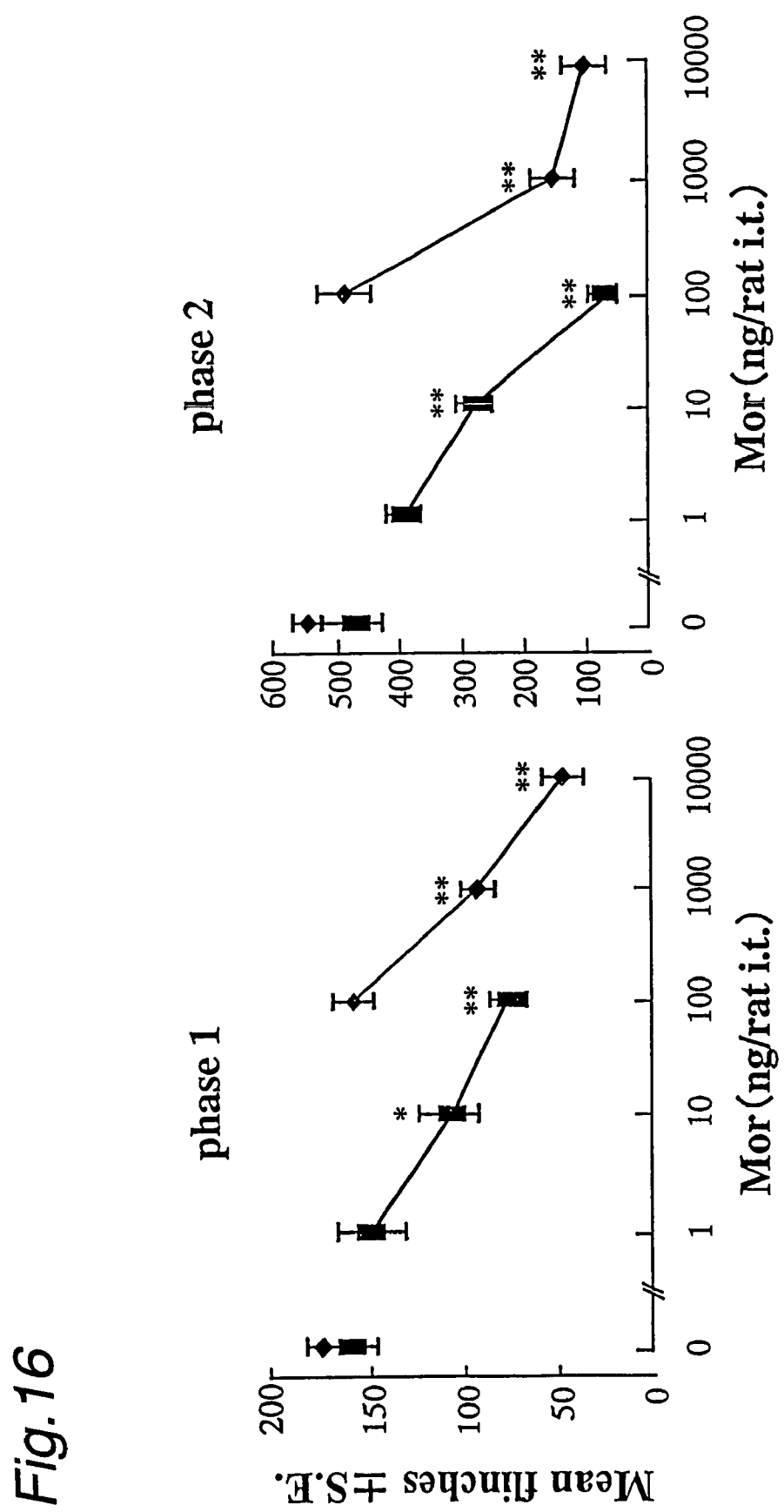
FIG. 16 is graphs showing the effect by lactoferrin of enhancing the analgesic effect of morphine, ■ representing co-administration of morphine and lactoferrin, ● administration of morphine alone, *$P<0.05$, **$P<0.01$ (vs. control, Dunnett's test)

As is apparent from FIGS. 16, the administration of lactoferrin can enhance the analgesic effect of morphine several 10- to 100-fold or more both in the first and phase 2 pains.

Example 14

The concentration of lactoferrin in blood after orally administering enteric coated tablets of lactoferrin was measured by ELISA using anti-bovine lactoferrin antibody.

[Measurement of Lactoferrin by ELISA]
1. 100 μl/well of a 500-fold dilution (2 μg/ml) of anti-bovine lactoferrin antibody (Goat, anti-bovine LF affinity purified, Bethyl Lab.) made with 0.05 M carbonate buffer solution (pH: 9.6) was put into a 96-well flat-bottom microplate (NUNC) and adsorbed at 4° C. over night.
2. The plate was washed with 0.05% Tween 20-phosphate buffer solution (PBS) three times. 300 μl of 1.3% gelatin-containing PBS, as a blocking agent, was put into the plate and incubated at room temperature for 30 minutes.
3. The plate was washed with 0.05% Tween 20-PBS three times. And 100 μl/well of a standard or sample having been diluted with PBS that contains 0.05% Tween 20, 0.5 M NaCl and 1% bovine serum albumin (BSA) (hereinafter referred to as NB-PBS) was put into the plate, incubated at 4° C. for 8 hours.
4. The plate was washed with 0.05% Tween 20-PBS three times. 100 μl/well of a 1000-fold dilution of anti-bovine lactoferrin antibody (Rabbit, anti-bovine LF, IgG grade, Yagai Corporation) made with NB-PBS was put into the plate and incubated at 4° C. for 8 hours.
5. The plate was washed with 0.05% Tween 20-PBS three times. 100 μl/well of a 5000-fold dilution of peroxidase-labeled anti-rabbit IgG antibody (Goat, anti-rabbit IgG, American Quail International) made with NB-PBS was put into the plate and incubated at 4° C. for 8 hours.
6. The plate was washed with 0.05% Tween 20-PBS three times. Then, 100 μl/well of 2,2-azino-bis(3-ethyl-benzothiazoline-6-sulfonic acid) Diammo salt (1.18 mM, Sanko Junyaku Co., Ltd.) dissolved in phosphate buffer solution, as a substrate solution, was put into the plate and incubated at 37° C. for 1 hour.
7. The absorbance was measured at 405 nm in a microplate reader (Sunrise Series, Type Classic, Chikan) and the concentration of lactoferrin was calculated using a calibration curve made with a standard.

Figure 17A:
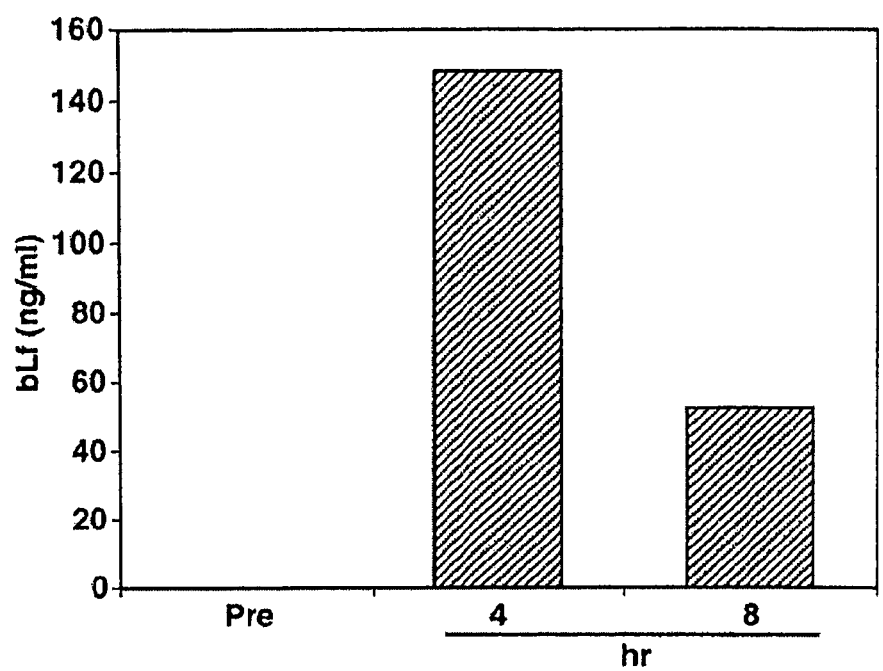
FIG. 17A is a graph showing the blood lactoferrin level when lactoferrin-containing enteric coated tablets were orally administered (Example 14) and FIG. 17B shows a schedule of administration of lactoferrin-containing enteric coated tablets and blood collection.

When 18 enteric coated tablets of lactoferrin (Production Example 5) (900 mg/60 kg=15 mg/kg) were administered to a male weighing 60 kg, lactoferrin was confirmed in the bloods collected 4 hrs and 8 hrs after the administration (FIG. 17A).

Figure 17B:
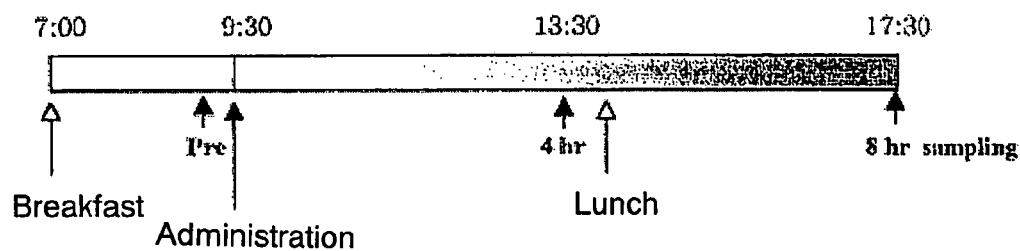

The administration of enteric coated tablets of lactoferrin and the collection of blood were performed on the following schedule. After breakfast at 7:00, the blood before administering lactoferrin was collected a little before 9:30 (Pre-sample), enteric coated tablets of lactoferrin (Production Example 4) were administered at 9:30, and the blood was collected at 13:30 and 17:30 (4 hr-sample and 8 hr-sample, respectively) (FIG. 17B).

The invention claimed is:

1. A method of alleviating pain by enhancing the analgesic action of an opioid in a patient with end stage cancer, said method comprising the steps of coating a dry and solid lactoferrin compound with a film forming agent to form an enteric coated lactoferrin compound; and administering to said patient a therapeutically effective amount of the enteric coated lactoferrin compound, wherein said enteric coated lactoferrin compound alleviates pain in said patient with end stage cancer.

2. The method according to claim 1, wherein the opioid is morphine.

3. The method according to claim 1, wherein the opioid is an endogenous opioid.

4. A method of alleviating pain in a patient with end stage cancer, the method comprising isolating a lactoferrin compound in a dry solid state; and administering to said patient an effective amount of the lactoferrin compound, wherein said lactoferrin compound alleviates pain in said patient with end stage cancer.

5. The method according to claim 4, wherein the method further comprises administering to said patient with end stage cancer an effective amount of an opioid.

6. The method according to claim 1, wherein the lactoferrin compound has a purity of greater than 98 percent.

7. The method according to claim 1, wherein the therapeutically effective amount of the enteric coated lactoferrin compound is administered orally.

8. The method according to claim 1, wherein the film forming agent is selected from the group consisting of shellac, polysorbate sorbitan, hydroxypropylmethylcellulose phthalate, carboxymethylethylcellulose, acetate phthalate cellulose, methacrylic copolymer, water insoluble ethylcellulose, and aminoalkylmethacrylate.

9. The method according to claim 1, wherein the lactoferrin compound is of bovine origin.

10. The method according to claim 1, wherein the lactoferrin compound is a recombinant lactoferrin.

11. A method of treating or alleviating pain in a patient with an end-stage cancer, said method comprising administering an effective amount of lactoferrin to said patient in need of such treatment or alleviation, wherein said lactoferrin treats or alleviates pain in said patient with an end-stage cancer.

12. A method of treating or alleviating pain in a patient with an end-stage cancer, said method comprising administering lactoferrin in an amount effective of enhancing the action of an opioid to said patient with an end-stage cancer, wherein said patient with an end-stage cancer has taken an opioid for treatment of pain.

13. A method of treating or alleviating at least one condition selected from the group consisting of pain and anxiety in a patient with an end-stage cancer, said method comprising administering an effective amount of lactoferrin to said patient in need of such treatment or alleviation, wherein said lactoferrin treats or alleviates pain and/or anxiety in said patient with an end-stage cancer.

14. The method of claim 11, wherein the patient has taken morphine.

15. A method of treating or alleviating at least one condition selected from the group consisting of pain and anxiety in a patient with an end-stage cancer, the method comprising administering an effective amount of lactoferrin to said patient with an end-stage cancer, wherein said patient with an end-stage cancer has taken an opioid for treatment of pain or anxiety.

16. A method of treating or alleviating pain or anxiety in a mammal with an end-stage cancer, said method comprising administering an effective amount of lactoferrin that enhances the action of an endogenous opioid produced by nociception in said mammal with an end-stage cancer.

17. The method according to claim 1, wherein the enteric coated lactoferrin compound is made into a dosage form while being kept in the dry solid state.

18. The method according to claim 11, wherein the lactoferrin is enteric coated and made into a dosage form in a dry solid state.

19. The method according to claim 1, wherein the enteric coated lactoferrin compound is prepared by mixing lactoferrin compound with an excipient, a binder and a disintegrating agent; slug-compacting the mixture with a slugging machine to form a large thin flat disk; crushing the disk; sieving the crushed disk to obtain lactoferrin granules of a uniform size; making lactoferrin tablets from said lactoferrin granules; and spraying an enteric-coating onto the lactoferrin tablets, while keeping the lactoferrin compound in a dry solid state.

20. The method according to claim 1, wherein the lactoferrin compound is obtained from bovine milk.

\* \* \* \* \*